United States Patent [19]

Masuhara

[11] Patent Number: 4,810,469
[45] Date of Patent: Mar. 7, 1989

[54] METHOD FOR STERILIZING ARTIFICIAL ORGANS AND APPARATUS USED THEREFOR

[75] Inventor: Shohei Masuhara, Toyonaka, Japan

[73] Assignee: Kanegafuchi Kagaki Kogyo Kabushiki, Osaka, Japan

[21] Appl. No.: 724,212

[22] Filed: Apr. 17, 1985

[51] Int. Cl.$^4$ ............................................. A61L 1/00
[52] U.S. Cl. ........................................ 422/26; 422/38
[58] Field of Search .................................. 422/26–28, 422/38

[56] References Cited

U.S. PATENT DOCUMENTS

| | | | |
|---|---|---|---|
| 3,910,761 | 10/1975 | Hopkins | 422/108 |
| 4,148,606 | 4/1979 | Morita et al. | 422/23 |
| 4,176,156 | 11/1979 | Asanuma et al. | 422/26 X |
| 4,376,051 | 3/1983 | Isono | 422/25 X |
| 4,411,866 | 10/1983 | Kanno | 422/25 |
| 4,673,506 | 6/1987 | Henne et al. | 422/26 X |

FOREIGN PATENT DOCUMENTS

| | | | |
|---|---|---|---|
| 55-01876 | 9/1980 | Japan | 422/26 |
| 0036340 | 9/1980 | Japan | 422/26 |

Primary Examiner—Barry S. Richman
Assistant Examiner—Lynn M. Kummert
Attorney, Agent, or Firm—Armstrong, Nikaido, Marmelstein & Kubovcik

[57] ABSTRACT

A method for sterilizing an artificial organ with high pressure steam in an autoclave which comprises passing a sterilized high temperature liquid maintained at a temperature sufficient for the sterilization through the artificial organ, thereby raising the inner temperature of the artificial organ approximately to a sterilization temperature, heating the artificial organ externally to a sterilizing temperature and maintaining that temperature for a predetermined time to sterilize the artificial organ, and passing a sterilized low temperature liquid through the artificial organ to cool it from the inside thereof, while cooling the artificial organ from the outside thereof. The sterilized low temperature liquid is one sterilized thermally followed by cooling, and in a preferable embodiment, the sterilized high temperature liquid is cooled and then introduced into the artificial organ. The sterilizing method is carried out, for instance, by using a high pressure steam sterilization apparatus provided with a storage tank for supplying the sterilized high temperature liquid to an artificial organ accommodated in a high pressure steam sterilizing environment, and a cooling means for cooling the sterilized high temperature liquid, the cooling means being disposed in a pipeline connecting the artificial organ with the storage tank.

4 Claims, 2 Drawing Sheets

METHOD FOR STERILIZING ARTIFICIAL ORGANS AND APPARATUS USED THEREFOR

BACKGROUND OF THE INVENTION

The present invention relates to a method for sterilizing artificial organs and an apparatus used therefor.

In recent years, a rapid progress in artificial organs, the most typical of which is an artificial kidney, has been made and apparatuses such as the artificial lung, artificial liver using an activated charcoal adsorbent, ascites-treating apparatus, and plasma separator are put to practical use. Also, a variety of other therapeutic devices utilizing adsorbents such as adsorbing elements and adsorbing agents have been developed, as disclosed in Japanese Unexamined Patent Publication (Tokkyo Kokai) No. 75141/1982, No. 27559/1983, No. 10055/1983, No. 12656/1983 and No. 197255/1984.

Generally these artificial organs and therapeutic devices are sterilized in the final stage of manufacturing, aseptically sealed, and then provided to the users. The most common method of sterilization used in recent years is sterilization with high-pressure steam in an autoclave. Other methods involve the use of an aqueous solution of formaldehyde or ethylene oxide gas, or irradiation with gamma-rays. However, since in these latter methods the sterilant tends to remain in the product even at the time of use or to cause degradation of the housing of artificial organs, they are not preferred in practice from the safety point of view.

Also, conventional heat-sterilizing methods wherein high-pressure steam or high-temperature water is applied to artificial organs from the outside thereof, are disadvantageous in the following points. If artificial organs contain, as internal packings or fillers, packing fluids such as water, physiological saline water and an aqueous solution containing a stabilizer or other additives, all of which have large heat capacities, or solid packings (including packing or filling agents and materials) having a low thermal conductivity, it takes a long time to heat the portion of the internal packings or fillers in the vicinity of the center of the artificial organs to a prescribed sterilizing temperature or to cool it down after sterilization. Moreover, since the outer part of the artificial organs is heated to an unnecessarily high temperature or exposed to the high sterilizing temperature for an unnecessarily long period of time, there occur fatal defects such as degradation of the housing and internal packing and elution of harmful substances.

It is an object of the present invention to provide a method for sterilizing artificial organs which is free of the above-mentioned disadvantages.

Another object of the present invention is to provide a sterilizing apparatus used for practicing the method.

These and other objects of the present invention will become apparent from the description hereinafter.

SUMMARY OF THE INVENTION

In accordance with the present invention, there is provided a method for sterilizing an artificial organ with high pressure steam in an autoclave, which comprises passing through an artificial organ a sterilized high temperature liquid having a temperature high enough to sterilize the artificial organ, thereby raising the inner temperature of the artificial organ substantially to a sterilizing temperature, heating the artificial organ externally to a sterilizing temperature with high pressure steam for a predetermined time to sterilize the artificial organ, and passing a sterilized low temperature liquid through the artificial organ, thereby lowering the inner temperature of the artificial organ.

The sterilization method of the present invention can be effectively practiced using a sterilizing apparatus comprising a pressure vessel for sterilizing an artificial organ with high pressure steam, a tank for holding a sterilized high temperature liquid used for heating the artificial organ from the inside thereof, a pipeline connecting the tank and the artificial organ accomodated in the pressure vessel, and a heat exchanger disposed in the pipeline.

In the method of the present invention, a sterilized liquid having a temperature high enough to sterilize an artificial organ (the sterilized liquid being hereinafter referred to as "sterilized high temperature liquid") is used to rapidly raise the inner temperature of the artificial organ to a high temperature capable of substantially sterilizing the inside of the artificial organ, in addition to high pressure steam for externally heating the artificial organ as in a conventional sterilization method. After heating the artificial organ to substantially a sterilizing temperature from both the inside and outside thereof, the artificial organ is maintained at the sterilizing temperature for a predetermined period of time enough to achieve sterilization. Preferably, the inside of the artificial organ should be maintained at a temperature enough to sterilize it also during the sterilization, and this can be attained, for instance, by the high pressure steam heating from the outside of the artificial organ. Accordingly, after the inner temperature has reached a high temperature capable of substantially sterilizing the inside of the artificial organ, the sterilized high temperature liquid introduced into the artificial organ may be discharged therefrom. In this sense, the expression "passing the sterilized high temperature liquid through an artificial organ", as used in the specification and claims, means introduction of the sterilized high temperature liquid into the artificial organ followed by holding it in the organ, repeated introduction at intervals, continuous passing of the sterilized high temperature liquid through the artificial organ, and other equivalent operations. Also, the heating by the sterilized high temperature liquid and the heating by high pressure steam may be carried out simultaneously or in a successive manner. Further, after raising the inner temperature of the artificial organ to a desired high temperature, the sterilized high temperature liquid may be discharged from or retained in the artificial organ, or may be successively fed to the organ during the sterilization.

The sterilized high temperature liquid is prepared usually by thermally sterilizing a liquid suitable for use in sterilization of an artificial organ, e.g. water, physiological saline water or an aqueous solution of a small amount of a stabilizer dissolved in water or physiological saline water, under temperature and time conditions necessary for the sterilization, e.g. 30 minutes at 115° C, 20 minutes at 121° C or 15 minutes at 126° C. The thus sterilized liquid of high temperature is immediately provided to the sterilization of artificial organs, or is held once in a suitable container at a temperature high enough to sterilize the artificial organs, usually at a temperature of not less than 105° C, and provided to the sterilization of artificial organs.

After completing the sterilization by maintaining the artificial organ at a sterilizing temperature for a predetermined time, a sterilized low temperature liquid is passed through the artificial organ to rapidly lower the inner temperature of the organ, while externally cooling the artificial organ. It is necessary that the liquid passed through the artificial organ for cooling is in the sterile state. The sterilized low temperature liquid is prepared by cooling a thermally sterilized hot liquid in advance of introduction into the sterilized artificial organ. As the sterilized hot liquid, there are employed the above-mentioned sterilized high temperature liquid which may be the same one as that used for the sterilization or may be one prepared separately and provided from a different source: and a liquid prepared in the same manner as the above-mentioned sterilized high temperature liquid and maintained at a temperature which does not permit growth of microorganisms, usually at a temperature of not less than 70° C, preferably not less than 80° C.

DETAILED DESCRIPTION

Figure 1:
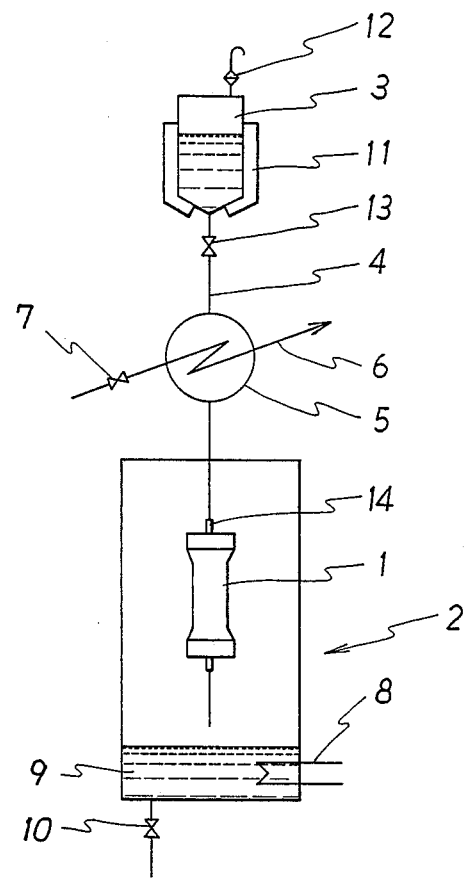
FIG. 1 is a flow diagram showing an embodiment of the sterilizing apparatus of the present invention.

In one embodiment of the sterilizing method according to the present invention, a sterilized high temperature liquid (which is generally water, physiological saline water or an aqueous solution containing appropriate amounts of a stabilizer or other additives) at a sufficiently high temperature to destroy microorganisms which contaminate the inner part of an artificial organ to be sterilized or a solid or liquid internal packing material packed within the artificial organ, is passed through the organ via a cooler (i.e., a heat exchanger) not functioning currently as a cooling means, (i.e., in the condition that it is not supplied with a cooling medium), thereby raising the temperature of the inner part of the artificial organ and the temperature of the internal packing material to approximately a sterilizing temperature, while the artificial organ is externally heated and maintained at a sterilizing temperature by means of heat. e.g. high pressure steam, applied from the outside of the organ for a necessary sterilizing time. The heating from the inside of the organ by the sterilized high temperature liquid may be conducted before or after or simultaneously with the high pressure steam sterilization. After the sterilization, a sterilized hot liquid is passed through the above-mentioned cooler functioning currently as a cooling means, for example, in the condition supplied with a cooling medium, in order to cool to a temperature not exceeding about 50° C. Subsequently, the resulting cold liquid (hereinafter referred to as "sterilized low temperature liquid") is passed through the artificial organ, whereby the artificial organ is rapidly cooled.

Compared with a conventional sterilizing method wherein the thermal sterilization of an artificial organ is effected by means of high temperature water or high pressure steam applied from the outside of the organ or a conventional method wherein the cooling of the inner part of the artificial organ relies on spontaneous cooling without resorting to a sterilized low temperature liquid, the method of the present invention is advantageous in that it overcomes the aforementioned disadvantages, i.e. prolonged heating and cooling times, sterilization at an unnecessarily high temperature, and deterioration in quality and performance of internal packings, etc. due to sterilization at an unnecessarily high temperature or a protracted maintenance at a high temperature over an unnecessarily long time. Furthermore, since a sterilized hot liquid is cooled and is immediately passed as the sterilized low temperature liquid through an artificial organ in order to cool it, the sterility of the sterilized low temperature liquid is fully assured.

A further advantage of the invention is that the sterilizing procedure is simple. Still further advantages of the invention are that the sterilized low temperature liquid can be used as the internal packing or filling material for artificial organs without any treatments and that no countermeasures are required for the thermal expansion of the packing liquid during heat sterilization and the contraction thereof during cooling. Of course, the outer surface of the artificial organ is also simultaneously sterilized.

Referring to the above-mentioned sterilized high temperature liquid having a sufficiently high temperature to sterilize an artificial organ, it depends on the kinds of microorganisms to be controlled, but the liquids and temperatures specified in the Japanese Pharmacopeia may be adopted. Generally, pressurized high temperature water, physiological saline water or aqueous solutions containing appropriate amounts of a stabilizer or other additives at a temperature not below 105° C are useful and, for most kinds of microorganisms, a temperature in the range of 115° to 130° C is employed. The sterilized hot liquid means a liquid which has once been heated to a sterilizing temperature for a necessary time for the sterilization thereof and is to be converted into the sterilized low temperature liquid used for cooling the artificial organ. It need not necessarily be at a temperature as high as the sterilized high temperature liquid used for heating the artificial organ, but may be a sterilized liquid having a temperature of 70° to 95° C obtained by lowering the temperature of a tank holding the sterilized high temperature liquid referred to just above, e.g. ordinary pressure hot water, physiological saline water or an aqueous solution containing appropriate amounts of a stabilizer or other additives.

The sterilized high temperature liquid for heating an artificial organ from its inside and a packing filled therein and the sterilized hot liquid for providing the sterilized low temperature liquid may be a liquid available immediately after heating to a sterilizing temperature for a necessary time for sterilization or a liquid which has once been heated to such temperature and then stored in a suitable container at a temperature which does not permit growth of microorganisms (e.g. not less than 70° C, preferably not less than 80° C), for a comparatively short time (e.g. not more than 24 hours). As stated above, the sterilized high temperature liquid may be used as the sterilized hot liquid which is cooled to provide the sterilized low temperature liquid. That is to say, the both liquids may be the same liquid supplied from the same storage tank. Also, they may be supplied under different conditions or from different containers within the sterilizing conditions set forth hereinbefore, e.g. one being supplied from a tank held at 121° C. and the other being supplied from a tank maintained at 80° C.

The internal packings of the artificial organ include a variety of solid materials, e.g. adsorbent materials or membranes, and aqueous media capable of coexisting therewith, e.g. solutions of stabilizers adopted to preserve and maintain the utility and shapes of the solid packing materials.

As the cooler or cooling device for cooling the sterilized hot liquid, there can be employed known liquid-liquid or gas-liquid heat exchangers and other equivalent devices of the types such as serpentine-tube, double tube and plate types.

While the aforementioned sterilized high temperature liquid and sterilized hot liquid are respectively passed through this cooler device before being introduced into the artificial organ, the passing of the sterilized high temperature liquid through the cooler device is intended to sterilize the cooler device as well. In this sense, the cooling of the sterilized hot liquid through the cooler device includes not only the mode of embodiment in which the sterilized high temperature liquid or the sterilized hot liquid flows through the cooler device and, then, into the artificial organ, but also the mode of embodiment in which, for example, a cooling medium line passes through the tank holding the sterilized high temperature liquid or otherwise the cooler device is located in the sterilized high temperature liquid tank or in the sterilized hot liquid tank. After all, it is preferable that the cooler device for cooling the sterilized hot liquid is, in its non-cooling mode, in sufficient contact with the sterilized high temperature liquid.

The cooling medium may be a liquid cooling medium such as city water, industrial water or other cooling water, or a low-temperature gas such as air.

In one embodiment of the present invention, a sterilized high temperature liquid prepared by heating to a high temperature necessary and sufficient for the sterilization thereof and maintaining at that temperature for a necessary time (for example at least 20 minutes at 121° C.) is passed through the inner part of an artificial organ in a high-pressure steam environment for sterilizing the artificial organ, thereby heating the organ from the inside and outside thereof concurrently. Accordingly, internal packing within the organ can be heated uniformly, irrespective of the location thereof within the artificial organ, to a prescribed temperature in a short time. Then, the above temperature is maintained for a sufficient time to effect sterilization (for example, 20 minutes at 121°). After the completion of the sterilization, the sterilized high temperautre liquid is passed through a cooler device to aseptically cool it down to a temperature of 50° C. or thereabout to give a sterilized low temperature liquid which is then passed through the artificial organ, whereby in association with the cooling of the organ from the outside thereof after withdrawal of the high pressure, high temperature environment, both the artificial organ and the internal packing therein are cooled in a short time.

Referring now to the artificial organ sterilizing apparatus according to the present invention, one preferred embodiment thereof is described below. The apparatus of the invention comprises a high pressure, high temperature sterilizing unit such as autoclave adapted to accommodate an artificial organ containing an internal solid packing material such as an adsorbent or a membrane and/or a liquid packing material used for retaining the performance and shape of the solid packing material, a sterilized high temperature liquid tank for holding a sterilized liquid heated at a sufficiently high temperature to destroy microorganisms contaminating the inner part of the artificial organ and the solid and liquid packing materials, and a pipeline connecting the high pressure, high temperature sterilizing unit with the sterilized high temperature liquid tank, and a heat exchanger disposed in the pipeline and equipped with an on-off valve or other means for admitting or suspending a flow of a cooling medium for cooling the sterilized high temperature liquid to the heat exchanger.

In another embodiment of the present invention, a three-way valve or equivalent flow switching means is provided in a pipeline connecting the artificial organ disposed in the high pressure sterilizing environment with the sterilized high temperature liquid storage tank. One of the three branches of the three-way switching means communicates with the high temperature liquid tank, another branch communicates directly with the artificial organ, and still another branch communicates with the artificial organ through a heat exchange device adapted to rapidly lower the temperature of the sterilized high temperature liquid by passing therethrough a cooling medium. The term "sterilized high temperature liquid storage tank" as used herein comprehends an equipment which can produce the sterilized high temperature liquid.

The sterilizing method and apparatus of the present invention will be described in further detail by referring to the preferred embodiments illustrated in the accompanying drawings. It should, however, be understood that the present invention is not limited to these embodiments.

Figure 2:
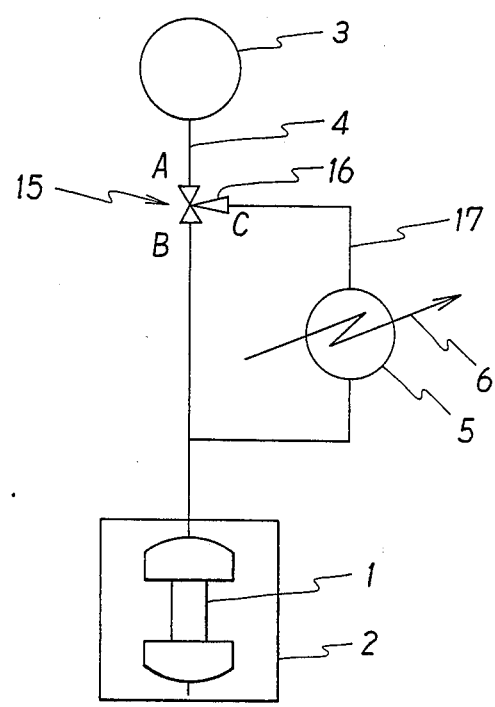
FIG. 2 is a flow diagram showing another embodiment of the sterilizing apparatus of the present invention.

FIGS. 1 and 2 are schematic diagrams showing embodiments of the invention. Referring, first, to FIG. 1, reference numeral 1 represents an artificial organ which may contain therein a solid packing material such as an adsorbent, a mixture of a solid packing material and a liquid packing material, or the like, and is accommodated in a high pressure steam sterilizing device. Reference numeral 3 represents a sterilized high temperature liquid storage tank for holding a sterilized high temperature liquid at a sufficiently high temperature to destroy the microorganisms contaminating the interior of the artificial organ, the solid packing material and the packing liquid, and it is connected with the artificial organ 1 by a pipeline 4. A heat exchanger 5 is interposed in the pipeline 4, and a coolant pipeline 6 for cooling medium such as cold water or cold air extends through the heat exchanger 5. Interposed in the pipeline 6 is an on-off control means 7 for controlling the flow of the cooling medium flowing through the pipeline 6.

The above-mentioned sterilizing unit 2 is equipped with a heater means 8, a high temperature liquid reservoir 9 and a drain valve 10. The high temperature liquid tank 3 is provided with a heating jacket 11 for heating the tank 3, and a respiratory filter 12 on the top thereof. The high temperature liquid tank 3 and the heat exchanger 5 are interconnected by a pressure resistant stainless steel pipe via a valve 13. The heat exchanger 5 and a circuit inlet 14 of the artificial organ 1 are connected by a pressure resistant stainless steel pipe at the portion between the heat exchanger 5 and the high pressure steam sterilizing unit 2 and, in the sterilizing unit 2, by a flexible heat resistant tube such as a heat resistant plastic tube.

The sterilized high temperature liquid storage tank 3 is filled with a liquid such as water, physiological saline water or a stabilizer-containing aqueous solution, which is preferably the same liquid as the packing liquid filled in the artificial organ, and then heated through the jacket means 11 to a sufficiently high temperature to make a sterilized high temperature liquid. The sterilizing conditions for preparing the sterilized high temperature liquid are preferably those prescribed in the Japanese Pharmacopeia, e.g. 30 minutes at 115° C., 20 minutes at 121° C., or 15 minutes at 126° C. The sterilized high temperature liquid may be prepared elsewhere and fed to the tank.

The sterilized high temperature liquid is maintained in the tank 3 at a temperature not less than the sterilizing temperature for the artificial organ. This sterilizing temperature is also preferably based on the Japanese Pharmacopeia.

Then, water in the high pressure sterilizing unit 2 is heated under pressure and the valve 13 is opened to admit the sterilized high temperature liquid in the storage tank 3 into the artificial organ 1 via the circuit inlet 14. A pump may be used in lieu of the valve 13. During this procedure, a controller 7 for heat exchanger 5 remains closed so that the cooling medium does not flow into the heat exchanger 5. Thus, the heat exchanger 5 does not function to exchange heat but lets the sterilized high temperature liquid from the tank 3 flow into the artificial organ 1, whereby the internal packing liquid is replaced with the high temperature sterile liquid, with the result that the internal temperature of the organ is elevated substantially to the heat sterilizing temperature. This replacement is conducted at least once and preferably 2 to 5 times. It is preferable that the time required for elevating the temperature of the high pressure steam sterilizing unit to the specified sterilizing temperature is previously measured and it is so arranged that the endpoint of the replacement of the liquid in the artificial organ 1 will coincide with the endpoint of the temperature elevation of the high pressure steam sterilizing unit.

When the above-mentioned replacement and the temperature elevation of the sterilizing unit 2 have been completed, the valve 13 is closed to conduct the sterilization of the artificial organ 1 for the specified time. After the completion of this sterilization procedure, the controller 7 is opened to admit the cooling medium into the heat exchanger 5 and the valve 13 is also opened. In this manner, the unpassed high temperature sterilized liquid, namely the sterilized liquid remaining in the tank 3, is cooled by the heat exchanger 5 and subsequently fed into the artificial organ 1 as a sterilized low temperature liquid in order to replace the hot liquid in the artificial organ, thus cooling the artificial organ, while cooling it from the outside thereof, for instance, by withdrawing the high pressure steam. This replacement for cooling is also conducted at least once, preferably 2 to 5 times.

By means of these procedures. the time required for heating and cooling the inner part of the artificial organ can be remarkably decreased. In a conventional sterilizing method wherein the heating of the artificial organ is conducted only from the outside thereof, it takes a long time to heat the center portion of the organ to a desired temperature after the temperature in the high pressure sterilizing unit 2 has reached the desired sterilizing temperature. For example, in case of an artificial organ having an inner diameter of 65 mm and packed with an adsorbent, the above-mentioned time is as long as 120 minutes. The same is true with the cooling time required. Therefore, when the artificial organ is heated by such a conventional technique so that even the center portion thereof is thermally sterilized, the artificial organ must be exposed to a high temperature for a prolonged time, thus resulting in deterioration of the material of the organ. According to the method of the present invention, the exposure time of the artificial organ to high temperature is minimized and accordingly such a problem is eliminated. Also, in the step of replacement for cleaning and cooling the artificial organ after sterilization, the maintenance of sterility is an important problem. In the method of the invention wherein the sterilized liquid consistently maintained under sterilizing conditions is cooled and supplied in a hermetically closed circuit, a complete sterility is assured.

Further, in case of heat-sterilizing an artificial organ packed with a packing or filling liquid, the damage of the organ due to thermal expansion of the filling liquid becomes a serious problem. In the method of the present invention, however, the thermal expansion is absorbed outside the artificial organ so that the above problem need not be taken into consideration.

The construction of another embodiment of the present invention wll be described below by referring to FIG. 2. The artificial organ 1 and the storage tank 3 are the same as those described and illustrated in FIG. 1.

The artificial organ 1 and storage tank 3 are interconnected by a pipeline 4. Disposed partway along the length of the pipeline 4 is a line switching means 16 adapted to divert the sterilized high temperature liquid emerging from the tank 3 at a three-way junction 15 in the direction of (A) to (B) or (A) to (C).

One (A) of the branches of the pipeline 4 communicates with the storage tank 3 and the other branch (B) to the artificial organ 1, while the third branch (C) communicates with the artificial organ 1 through a pipeline 17 and a heat exchanger 5 disposed intermediately in the pipeline 17.

The heat exchanger 5 is equipped with a coolant line 6 for a low-temperature water or other liquid or air so that heat exchange may take place between the coolant and the liquid flowing in the pipeline 17 and heat exchanger 5.

The operation of this apparatus is described below. First, the pipeline switching means 16 is set so that the liquid will pass in the direction of (A) to (B) but will not flow in the directions of (A) to (C) and (B) to (C). In this condition, the sterilized high temperature liquid from the storage tank 3 flows directly into the artificial organ 1 via the three-way junction 15, whereby the inner surface and packings of the artificial organ 1 are rapidly heated to a sterilizing temperature. Thereafter, the artificial organ 1 is sterilized with high pressure steam for a predetermined time.

After the completion of the high pressure steam sterilization, the switching means 16 is set so that the liquid will flow in the direction of (A) to (C) but will not flow in the directions of (A) to (B) and (B) to (C). whereupon the sterilized high temperature liquid from the storage tank 3 flows into the heat exchanger 5 via the pipeline 17. In the heat exchanger 5, the sterilized high temperature liquid undergoes heat exchange with the low-temperature water or other fluid or air, whereby the former is rapidly cooled and fed as the sterilized low temperature liquid into the artificial organ 1. Thus, the inner part of the artificial organ and the internal packing material are rapidly cooled.

By the above series of operations, the artificial organ 1 is rapidly heated by the heat applied from both the inside and outside of the artificial organ, and after the high pressure steam sterilization for a predetermined time, it is rapidly cooled from both the inside and outside.

In addition, nonuniformity in heating time and high-temperature retention time between the center portion and the outer portion of the artificial organ are also minimized.

In the above description of the embodiments illustrated in FIGS. 1 and 2, only the essential components have been explained. However, the whole apparatus shown in FIG. 1 or FIG. 2 may be housed in a single pressure housing (for example, a high pressure steam sterilizer) or constructed with the heat exchanger 5 and coolant line 6 externally disposed, or the above-mentioned controller 7 and/or switching means 16 may be replaced with automatic or remote-controllable valve means. Also, a plurality of the sterilized high temperature liquid storage tanks 3 or equipments for preparing the sterilized high temperature liquid may be arranged in parallel, or the sterilization apparatus may be constructed so that a plurality of artificial organs 1 are arranged in parallel and accordingly sterilized in one operation for increasing productivity. Futher, a pump for increasing the flow rate of the sterilized high temperature liquid flowing in the pipeline 4 or a flow regulator for controlling the flow rate thereof may be provided, or the apparatus may be constructed so that the artificial organ 1 and the storage tank are disposed at substantially the same level and a pump is disposed in the pipeline. The above and other modified arrangements may be adopted either singly or in a suitable combination. It is to be understood that these and other arrangements and modifications may be made in the invention without departing from the spirit and scope thereof.

What is claimed is:

1. A method for sterilizing an artificial organ in an autoclave, which comprises passing through an artificial organ having an inner and an outer surface a sterilized high temperature liquid having a temperature high enough to sterilize the artificial organ, thereby raising the temperature of the inner surface of the artificial organ substantially to a sterilizing temperature, heating the artificial organ externally to a sterilizing temperature with high pressure steam for a predetermined time to sterilize the artificial organ, and passing a sterilized low temperature liquid through the artificial organ, thereby lowering the temperature of the inner surface of the artificial organ.

2. The method of claim 1, wherein said sterilized low temperature liquid is formed by cooling said sterilized high temperature liquid which has not been passed through said artificial organ.

3. The method of claim 1, wherein the passing of the sterilized high temperature liquid is carried out simultaneously with the external heating of the artificial organ by high pressure steam, and after reaching the sterilizing temperature, the artificial organ is maintained at said sterilizing temperature for a time sufficient for sterilization to occur.

4. The method of claim 1, wherein the passing of the sterilized low temperature liquid is carried out simultaneously with external cooling of the artificial organ.

* * * * *

UNITED STATES PATENT AND TRADEMARK OFFICE
CERTIFICATE OF CORRECTION

PATENT NO. : 4,810,469
DATED : March 7, 1989
INVENTOR(S) : MATSUHARA

It is certified that error appears in the above-identified patent and that said Letters Patent is hereby corrected as shown below:

On the cover page, Item [73], "Kanegafuchi Kagaki Kogyo Kabushiki" should read --Kanegafuchi Kagaku Kogyo Kabushiki Kaisha--.

Signed and Sealed this

Twelfth Day of December, 1989

*Attest:*

JEFFREY M. SAMUELS

*Attesting Officer*     *Acting Commissioner of Patents and Trademarks*